United States Patent
Khanna

(10) Patent No.: US 9,950,098 B2
(45) Date of Patent: Apr. 24, 2018

(54) DEVICE AND METHOD FOR PERFORMING A DECOMPRESSIVE CRANIOTOMY

(76) Inventor: Rohit Khanna, Daytona Beach, FL (US)

(*) Notice: Subject to any disclaimer, the term of this patent is extended or adjusted under 35 U.S.C. 154(b) by 31 days.

(21) Appl. No.: 13/316,529

(22) Filed: Dec. 11, 2011

(65) Prior Publication Data

US 2012/0203284 A1    Aug. 9, 2012

Related U.S. Application Data

(60) Provisional application No. 61/422,640, filed on Dec. 13, 2010.

(51) Int. Cl.
*A61B 17/80* (2006.01)
*A61L 31/02* (2006.01)
*A61B 17/68* (2006.01)
*A61L 31/04* (2006.01)
*A61B 17/00* (2006.01)

(52) U.S. Cl.
CPC .......... *A61L 31/022* (2013.01); *A61B 17/688* (2013.01); *A61B 17/8004* (2013.01); *A61B 17/8061* (2013.01); *A61L 31/04* (2013.01); *A61B 2017/00004* (2013.01); *A61B 2017/00862* (2013.01)

(58) Field of Classification Search
CPC ... A61L 31/022; A61L 21/04; A61B 17/8061; A61B 17/688; A61B 17/8004; A61B 2017/0004; A61B 2017/08862
USPC ................. 606/280–299; 623/17.17–17.19
See application file for complete search history.

(56) References Cited

U.S. PATENT DOCUMENTS

| | | |
|---|---|---|
| 5,578,036 A | 11/1996 | Stone et al. |
| 5,707,373 A | 1/1998 | Sevrain et al. |
| 5,800,436 A | 9/1998 | Lerch |
| 5,902,304 A | 5/1999 | Walker et al. |
| 5,916,200 A | 6/1999 | Eppley et al. |
| 5,916,217 A | 6/1999 | Manthrop et al. |
| 5,993,448 A | 11/1999 | Remmier |
| 6,093,188 A * | 7/2000 | Murray .............. A61B 17/8085 606/282 |
| 6,187,004 B1 | 2/2001 | Fearon |
| 6,355,036 B1 | 3/2002 | Nakajima |
| 6,379,363 B1 | 4/2002 | Herrington et al. |
| 6,485,493 B1 | 11/2002 | Bremer |
| 6,585,739 B2 | 7/2003 | Kuras et al. |
| 6,685,707 B2 | 2/2004 | Roman et al. |
| 6,755,834 B2 | 6/2004 | Amis |
| 7,048,737 B2 | 5/2006 | Wellisz et al. |
| 7,229,441 B2 * | 6/2007 | Trieu ................. A61B 17/7022 606/279 |
| 7,361,178 B2 | 4/2008 | Hearn et al. |

(Continued)

FOREIGN PATENT DOCUMENTS

WO    WO-2012/082571 A2    6/2012

*Primary Examiner* — Christopher Beccia
(74) *Attorney, Agent, or Firm* — Wenderoth, Lind & Ponack, L.L.P.

(57) ABSTRACT

A fixation device comprises a first anchor portion being configured to join to a first bone portion. A second anchor portion is configured to join to a second bone portion. An intermediate component extends between the first anchor portion and the second anchor portion. The intermediate component is configured to expand and contract enabling constrained movement of the second bone portion.

20 Claims, 11 Drawing Sheets

(56) References Cited

U.S. PATENT DOCUMENTS

| | | |
|---|---|---|
| 7,387,633 B2 | 6/2008 | Ahmad et al. |
| 7,867,262 B2 | 1/2011 | Morales et al. |
| 8,206,425 B2 | 6/2012 | Khanna |
| 2004/0215192 A1* | 10/2004 | Justis ................. A61B 17/7011 606/257 |
| 2005/0107813 A1 | 5/2005 | Garcia |
| 2007/0185489 A1 | 8/2007 | Abdou |
| 2007/0238069 A1* | 10/2007 | Lovald ............... A61B 17/8071 433/173 |
| 2007/0293865 A1 | 12/2007 | Ko |
| 2008/0154312 A1 | 6/2008 | Colleran et al. |
| 2008/0200954 A1 | 8/2008 | Tucci |
| 2009/0024172 A1* | 1/2009 | Pizzicara ..................... 606/280 |
| 2011/0028972 A1 | 2/2011 | Khanna |
| 2011/0028973 A1 | 2/2011 | Khanna |
| 2012/0165879 A1 | 6/2012 | Khanna |
| 2012/0184999 A1 | 7/2012 | Khanna |

* cited by examiner

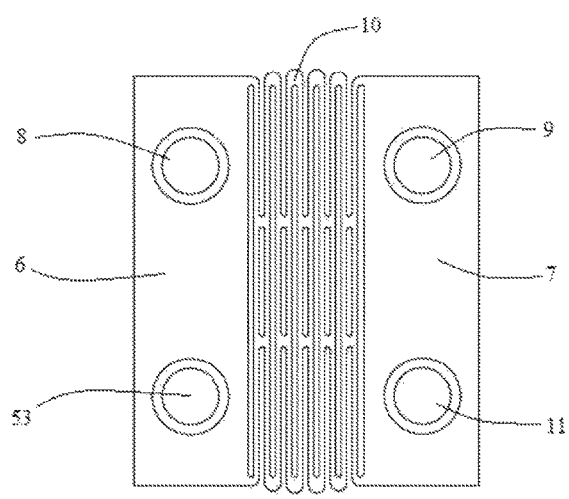
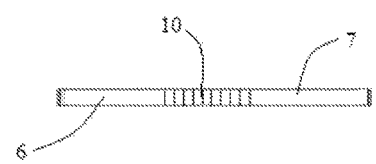
Fig. 5
Fig. 4
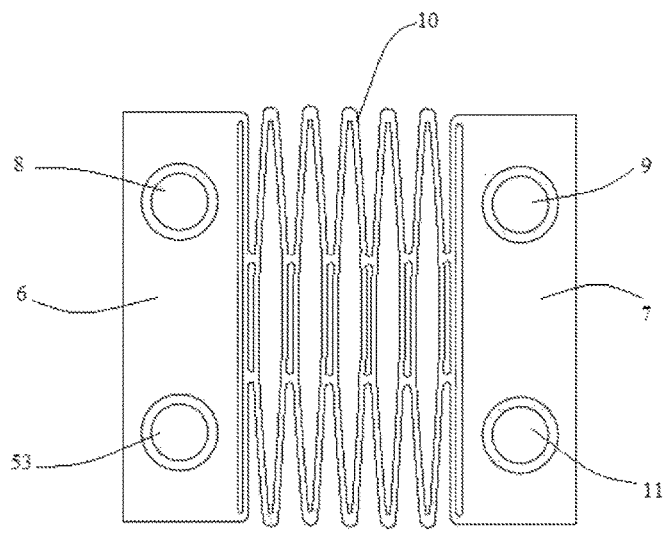
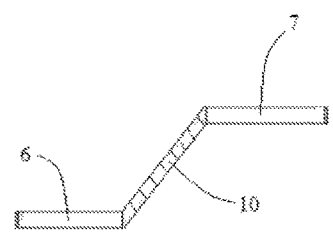
Fig. 7
Fig. 6

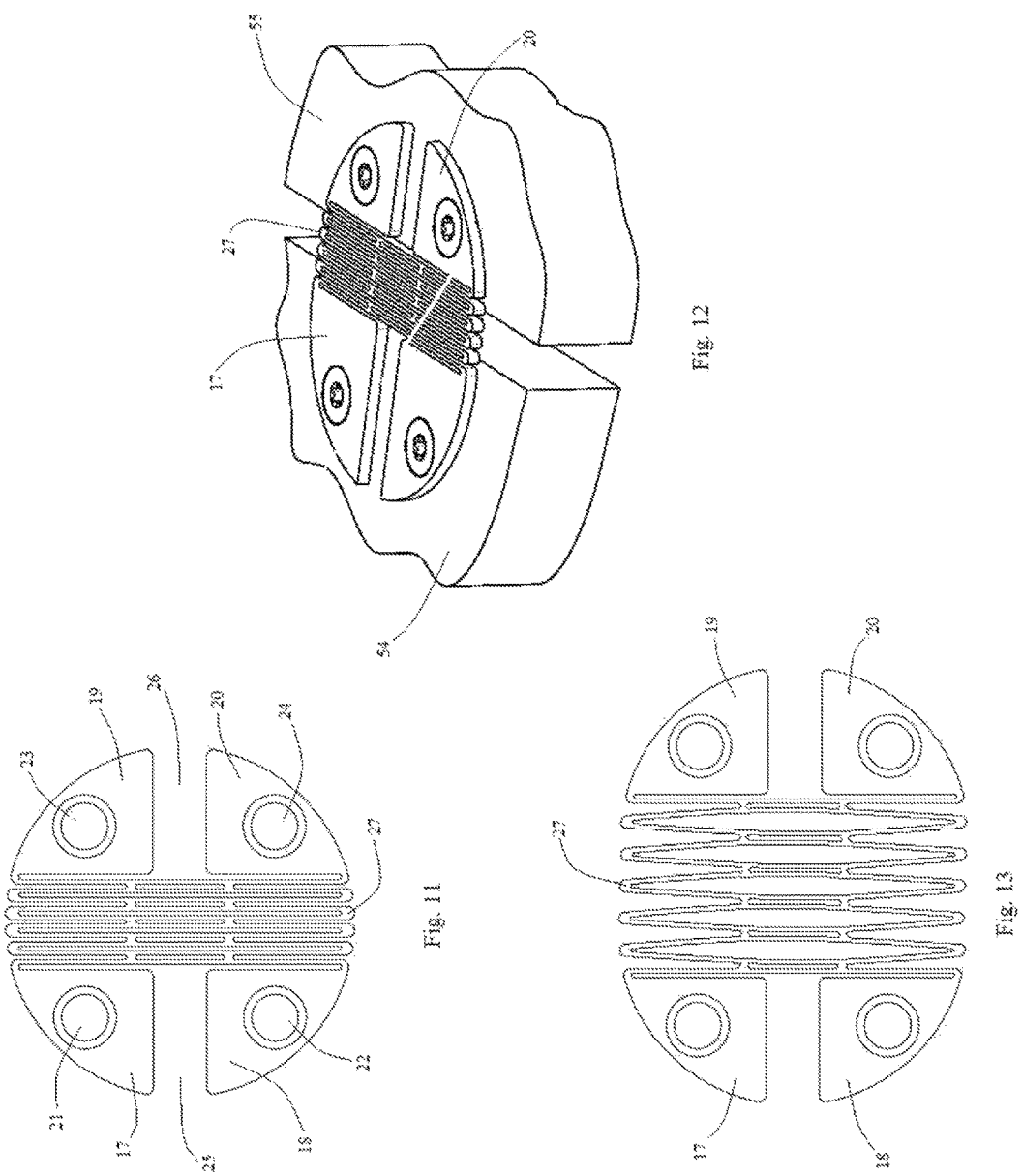

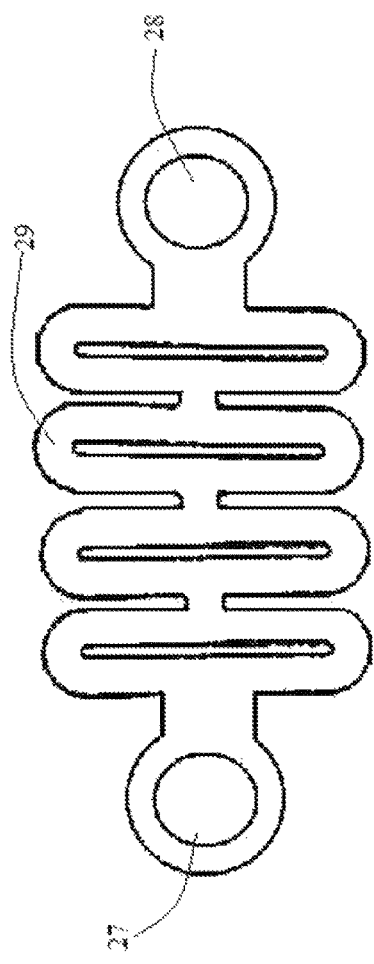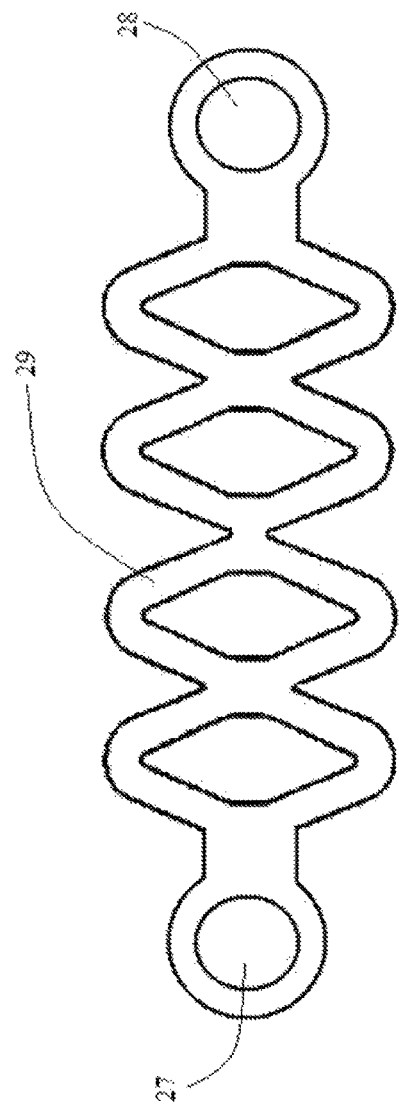

DEVICE AND METHOD FOR PERFORMING A DECOMPRESSIVE CRANIOTOMY

CROSS-REFERENCE TO RELATED APPLICATIONS

The present Utility patent application claims priority benefit of the U.S. provisional application for patent Ser. No. 61/422,640 entitled "Decompressive Craniotomy Device", filed on Dec. 13, 2010, under 35 U.S.C. 119(e). The contents of this related provisional application are incorporated herein by reference for all purposes to the extent that such subject matter is not inconsistent herewith or limiting hereof.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

One or more embodiments of the invention generally relate to medical devices. More particularly, one or more embodiments of the invention relate to a device and method for performing a decompressive craniotomy.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon. Neurosurgery routinely involves performing craniotomies for exposure of the brain and intracranial contents for various intracranial pathologies including, but not limited to, tumors, head injuries, vascular malformations, aneurysms, infections, hemorrhages, strokes, and brain swelling. A craniotomy typically involves the creation of burr holes and the removal of a portion of the skull (i.e., bone flap) with subsequent healing of the bone flap for closure.

By way of educational background, an aspect of the prior art generally useful to be aware of is that several methods and fixation devices are currently available for re-attaching the bone flap to the skull including small metallic or absorbable plates with screws or wires. Another current method is the use of cranial clamps consisting of two connected circular elements placed on the inside and outside surfaces of the skull. The aforementioned cranial fixation devices generally provide for a rigid fixation of the bone flap to the skull.

In cases of post-operative intracranial hemorrhaging and/or the development of brain swelling, a decompressive craniectomy is typically performed. A decompressive craniectomy is a neurosurgical procedure generally used to treat increased pressure within the skull, herein referred to as intracranial pressure (ICP), from causes such as, but not limited to, head injury, stroke, brain tumor, infection, cerebral hemorrhage, space occupying lesions, hypoxia, hypertension, aneurysm, arteriovenous malformation, venous sinus thrombosis, craniosynostosis, and hydrocephalus. The technique of performing a decompressive craniectomy often involves the removal of a portion of the skull and opening of the dura mater covering the brain, thereby allowing the swollen brain to herniate outwards through the surgical skull defect rather than downwards to compress the brainstem. The procedure generally improves outcomes by lowering ICP. Increased ICP is often debilitating or fatal because this pressure may result in compression of the brain and restriction of cerebral blood flow. A typical aim of a decompressive craniectomy is to reduce this pressure. In general, it is believed that the larger the bone flap, the more ICP is reduced. Following removal of the bone flap, the dural opening is typically closed with a patch graft taken from a cow, pig, cadaver, or a synthetic graft. A synthetic collagen matrix is often used as a graft since the matrix is capable of expanding. In addition to reducing ICP, studies typically have shown that a decompressive craniectomy may improve cerebral perfusion pressure and cerebral blood flow in patients with head injuries. A decompressive craniectomy may also be used in some cases to treat major strokes associated with malignant brain swelling and increased ICP. It is believed that a decompressive craniectomy typically improves survival and functional outcome in patients with severe brain swelling from causes such as, but not limited to, head injury or stroke if performed in a timely manner. There usually is an inherent time delay between diagnosing the cause of the increased ICP and performing a decompressive craniectomy. Typically, once a post-operative increase in ICP is detected, either through a clinical exam or an ICP monitoring device, medical treatment is initiated and CT or MRI imaging is obtained to identify the underlying cause of the increased ICP. If the need for another surgery or a decompressive craniectomy is identified, the anesthesiologist and operating room staff are notified and surgery is generally performed as promptly as possible. Unfortunately, at times the operating room and/or staff are unavailable, which may increase the time before the surgery can be performed. Despite the best of attempts by the surgeon, in some cases of massive brain swelling or a rapidly developing post-operative hemorrhage, this delay may result in irreversible brainstem injury and in some cases a consequent vegetative state or death.

After a craniectomy, it is believed that the risk of brain injury is increased because of the removed bone flap, particularly after the patient heals and becomes mobile again. In addition, there is often an obvious cosmetic skin deformity. Therefore, special measures are generally taken to protect the brain, such as, but not limited to, a helmet or a temporary implant in the skull. Other risks that may arise out of a craniectomy include, without limitation, infection, cerebrospinal fluid leakage, hydrocephalus, encephalomyocele, subdural hygroma and hemorrhage.

Once the patient has healed sufficiently, the craniectomy skull defect is usually closed with a cranioplasty. A cranioplasty typically involves the repair of a defect in the vault of the skull. This repair may be carried out by using bone removed in an earlier surgery that has been preserved or by using bone from elsewhere as a graft. Bone that may be used as a graft may include, without limitation, the iliac bone bounding the pelvis, ribs or a portion of adjacent skull bone. If possible, the original bone flap is generally preserved after the craniectomy in anticipation of the cranioplasty. The bone flap is usually stored sterilely in a freezer until the patient is ready for implantation of the bone flap into the craniectomy skull defect. Typically, this time period can last several months since it may take this long to treat the underlying cause of the increased ICP. This extended time period may result in the increased risk of brain injury and may also cause an increased risk of infection in the stored bone flap. Another technique of storing a removed bone flap typically involves placing the bone flap under the skin in the abdomen of the patient. This technique generally requires a surgical procedure to place the bone flap in the abdomen and another surgical procedure to remove the bone flap, thereby typically increasing consequent risks to the patient. In cases where the bone flap cannot be replaced due to infection or any other reason, the skull defect is generally repaired with a prosthetic plate or titanium mesh and bone cement. A prosthetic plate typically cannot completely replicate the original skull defect, and therefore some cosmetic deformity often persists following a prosthetic cranioplasty. The prosthesis may also increase the risk of infection. The risks associated with cranioplasty typically include, without limitation, infection, hemorrhage, brain injury, seizures, and death along with other risks inherent to any surgery and general anesthesia. It is also usually necessary for the patient to remain in the hospital for a week or so after a cranioplasty.

By way of educational background, another aspect of the prior art generally useful to be aware of is that some cranial fixation devices describe their use for distraction osteogenesis. Distraction osteogenesis is a surgical process used to reconstruct craniofacial deformities. The bone is fractured into two segments, and the two bone ends of the bone are gradually moved apart during the distraction phase, allowing new bone to form in the gap and reshape the length of the bone. When the desired length is reached, a consolidation phase follows in which the bone is allowed to solidify in the gap. For example, without limitation, one such device describes a telescopic bone plate for use in bone lengthening by distraction osteogenesis. The bone plate is attached to osteomically separated mandible or skull sections by a thread screw assembly. The extent of the required distraction can be adjusted by an external screwdriver. Another such device describes a skull fixation device typically used for the treatment of craniofacial deformities that provides for relative movement of the skull segments by a percutaneously placed external wrench. Yet another such device describes a mandible or skull expansion plate. The extent of the expansion is adjusted by an externally placed device. Another currently available skull expansion plate comprises a hinged plate at one end and a bone adjuster at the other end comprising two plates with a shaft. The shaft is operated externally to adjust the distance between the bone flap and the skull.

The aforementioned cranial fixation devices in the prior art provide for treatment of craniofacial defects, in particular craniosynostosis. These devices generally require an external screwdriver or other external adjustment means to control the extent of the skull movement allowed and do not typically describe or provide for outward or inward movement of the bone flap relative to the skull in response to a change in the ICP. These devices are also generally placed on the outer surface of the skull and have substantially high profiles which may result in increasing the risk of scalp irritation and palpable cosmetic deformities. One can expect that chronic scalp irritation may cause erosion and exposure of the device through the skin with consequent life threatening infections.

By way of educational background, another aspect of the prior art generally useful to be aware of is that there are multiple methods for performing a decompressive craniectomy. One method of performing a decompressive craniectomy involves attaching the bone flap to the skull with a hinged plate. This method describes attaching the hinged plate to one end of the bone flap and attaching the other end of the bone flap to a rigid plate or no plate at all. The described method typically involves another surgery to fixate the unconstrained bone flap at the rigid plate or plate free end to the skull once the brain swelling subsides. Another method describes a deformable plate which may be used instead of a hinged plate as the hone flap attachment. This construct also typically involves another surgery to fixate the unconstrained bone flap at the straight plate or plate free end of the bone flap. The end of the bone flap attached to the hinged or deformable plate is generally unable to move outwards, and therefore allows limited bone flap movement. Another method involves the use of a two part, sliding device for cranial fixation. This device protrudes outwards from the skull surface and may result in a cosmetic defect, overlying skin irritation, risk of erosion or infection, and typically requires another operation to remove the device once the bone flap heals to the skull.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which:

FIG. 1 is a diagrammatic top view. FIG. 2 is a perspective top view, FIG. 3 is a diagrammatic side view.

FIGS. 4 through 7 illustrate an exemplary cranial fixation device with a square shape, in accordance with an embodiment of the present invention. FIG. 4 is a diagrammatic top view of the device in a contracted position. FIG. 5 is a diagrammatic side view of the device in the contracted position. FIG. 6 is a diagrammatic top view of the device in an expanded position, and FIG. 7 is a diagrammatic side view of the device in an expanded position;

FIG. 8 is a diagrammatic top view of the device in a contracted position. FIG. 9 is a diagrammatic side view of the device in the contracted position, and FIG. 10 is a diagrammatic top view of the device in an expanded position;

FIGS. 11 through 13 illustrate an exemplary cranial fixation device with a circular shape, in accordance with an embodiment of the present invention. FIG. 11 is a diagrammatic top view of the device in a contracted position. FIG. 12 is a perspective side view of the device in the contracted position attached to a skull on one side and a bone flap on the other side. FIG. 13 is a diagrammatic top view of the device in an expanded position;

FIGS. 14 and 15 illustrate an exemplary cranial fixation device, in accordance with an embodiment of the present invention. FIG. 14 is a diagrammatic top view of the device in a contracted position, and FIG. 15 is a diagrammatic top view of the device in an expanded position;

FIG. 16 is a diagrammatic top view of the device in a contracted position, and FIG. 17 is a diagrammatic top view of the device in an expanded position;

FIG. 18 is a diagrammatic top view of the device in a contracted position, and FIG. 19 is a diagrammatic top view of the device in an expanded position;

FIG. 20 shows a brain in a non-swollen state, and FIG. 21 shows the brain in a swollen state;

FIG. 22 shows the normal position of the bone flap, and FIG. 23 shows the bone flap shifted outwards relative to the skull to accommodate an increase in the pressure inside the skull.

Figure 1:
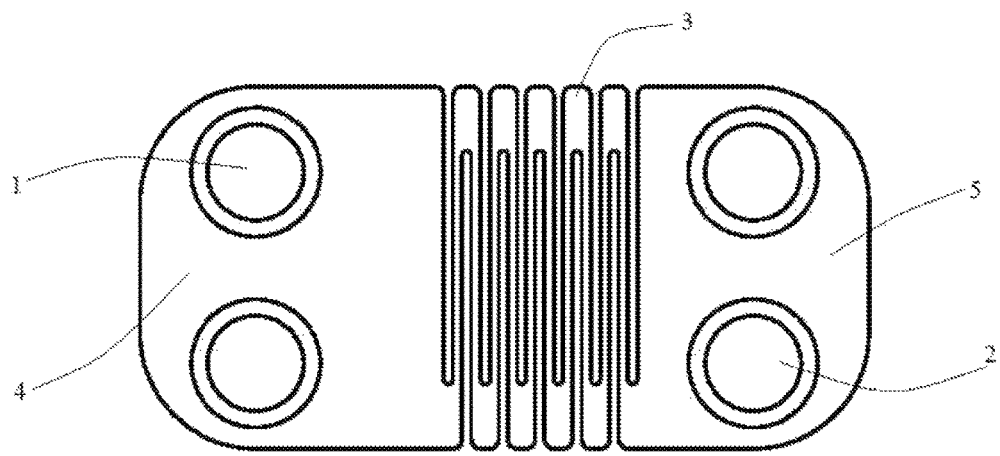
FIGS. 1 through 3 illustrate an exemplary cranial fixation device with a rectangular shape, in accordance with an embodiment of the present invention.

Unless otherwise indicated illustrations in the figures are not necessarily drawn to scale.

DETAILED DESCRIPTION OF SOME EMBODIMENTS

Embodiments of the present invention are best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

Considering the complexities and risks typically involved in the post-operative management of critically ill patients undergoing a craniotomy, a practical embodiment of the present invention provides a method and a cranial fixation device for fixing a bone flap to the skull following a craniotomy with immediate treatment of increased ICP that generally avoids the need for performing a subsequent cranioplasty. Many practical embodiments provide cranial fixation following a craniotomy with a fixation device that allows for constrained movement of the bone flap to immediately accommodate an increase in ICP and subsequently enables the bone flap to move inward toward the skull once the ICP normalizes. In many practical embodiments this fixation device is a flexible and expandable cranial fixation plate. In some practical embodiments, the cranial fixation device comprises spaced anchor portions and an intermediate component extending between the anchor portions which comprises a series of elastic tension spring members allowing for expansion and contraction. Since the decompressive procedure provided in many practical embodiments involves leaving the bone flap in place rather than removing the bone flap as is typically done in a decompressive craniectomy, this procedure is herein referred to as a decompressive craniotomy.

Figure 2:
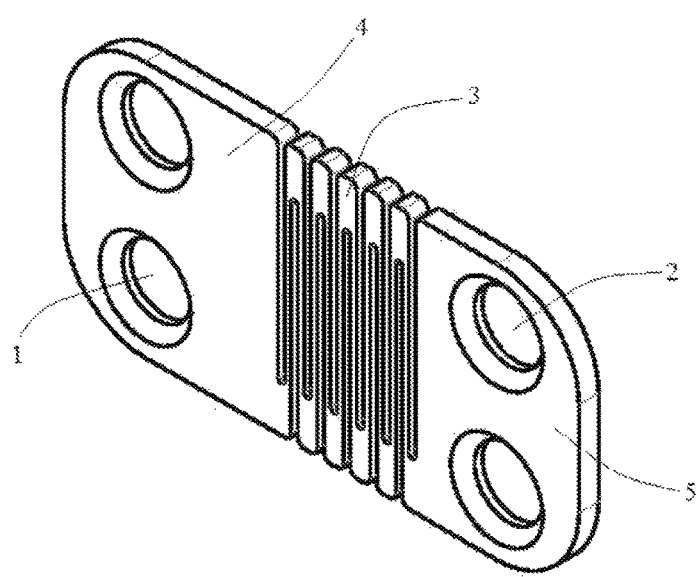
Figure 3:
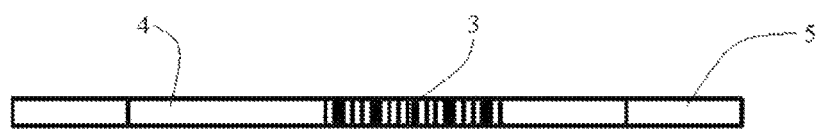
Figure 3A:
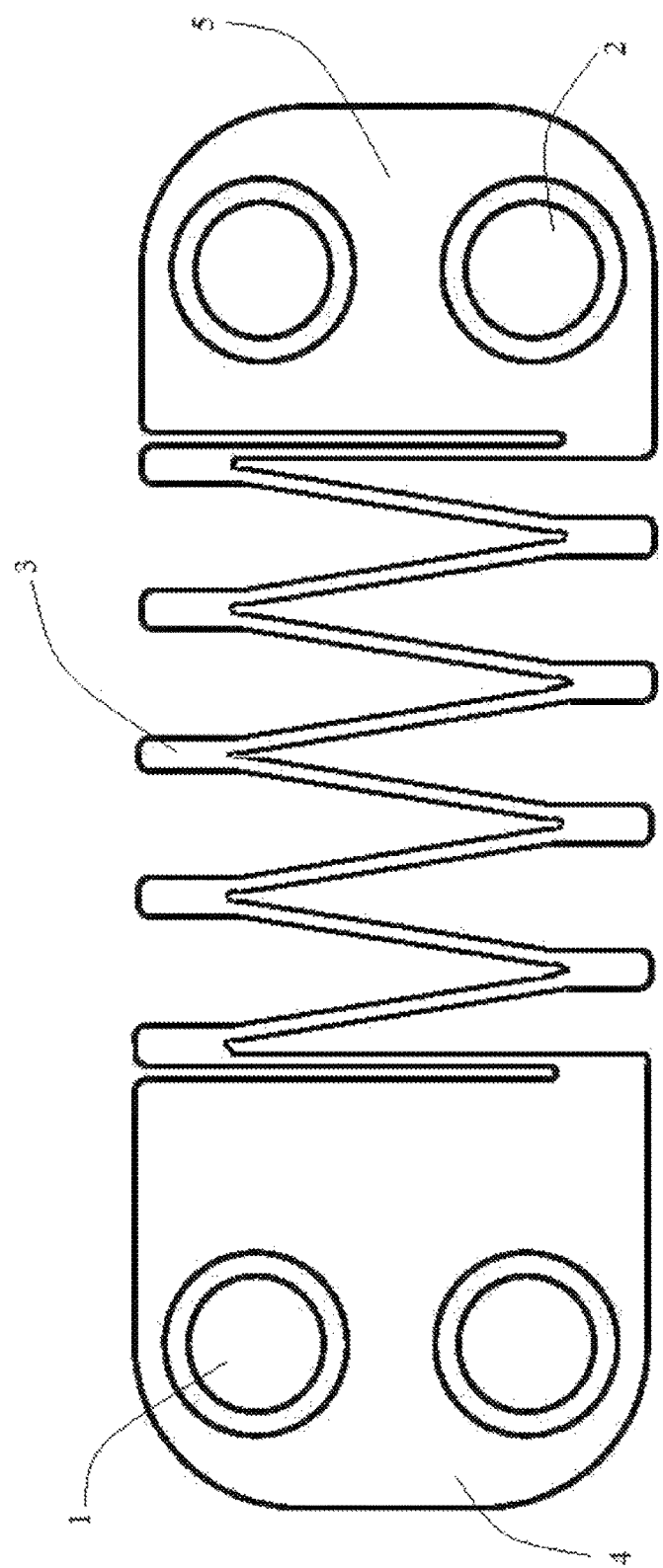
FIG. 3a is a diagrammatic top view.

FIGS. 1 through 3 illustrate an exemplary cranial fixation device with a rectangular shape, in accordance with an embodiment of the present invention. FIG. 1 is a diagrammatic top view of the device in a contracted position and FIG. 3a is a diagrammatic top view in an expanded position. FIG. 2 is a perspective top view, and FIG. 3 is a diagrammatic side view. In the present embodiment, the device comprises an anchor portion 4 with bone fastener holes 1 for attachment to a skull and an anchor portion 5 with bone fastener holes 2 for attachment to a bone flap. An intermediate component 3 comprises a series of elastic tension spring members that expand or contract depending on the ICP and allow outward movement of the bone flap relative to the skull. The tension spring members of intermediate component 3 comprise of a series of parallel, elastically deformable metal strips joined at the strip ends. The contracted position of intermediate component 3 is illustrated by way of example in FIGS. 1 through 3. With an increase in ICP within the skull to which the device is attached, the swollen brain exerts pressure on the bone flap forcing the elastic tension spring members of intermediate component 3 to expand and allow anchor portion 5 attached to the bone flap to move outward to accommodate the increase in ICP by increasing the skull space. With subsequent resolution of the brain swelling and normalization of the ICP, the expanded tension spring members of intermediate component 3 contract and return the bone flap to a position substantially even with the skull.

FIGS. 4 through 7 illustrate an exemplary cranial fixation device with a square shape, in accordance with an embodiment of the present invention. FIG. 4 is a diagrammatic top view of the device in a contracted position. FIG. 5 is a diagrammatic side view of the device in the contracted position. FIG. 6 is a diagrammatic top view of the device in an expanded position, and FIG. 7 is a diagrammatic side view of the device in an expanded position. In the present embodiment, a skull attachment anchor portion 6 comprises bone fastener holes 8 and 53, and a bone flap attachment anchor portion 7 comprises bone fastener holes 9 and 11. Anchor portions 6 and 7 are connected by an intermediate component 10 comprising a series of parallel tension springs which are elastically deformable strips joined together at the ends and the middle portions of the strips. Referring to FIG. 7, this expanded position of intermediate component 10 allows bone flap anchor portion 7 to move upward relative to skull anchor portion 6.

Figure 8:
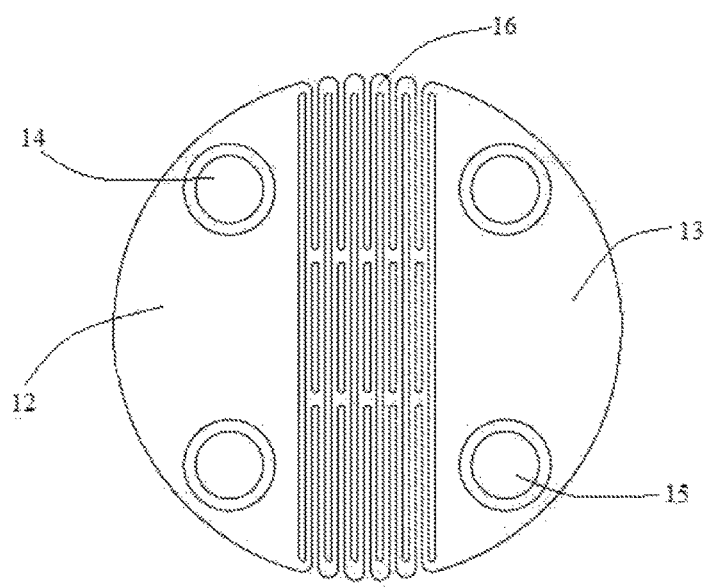
FIGS. 8 through 10 illustrate an exemplary cranial fixation device with a circular shape, in accordance with an embodiment of the present invention.
Figure 9:
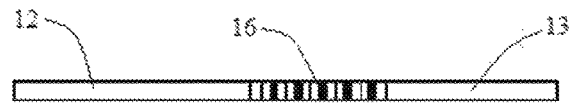
Figure 10:
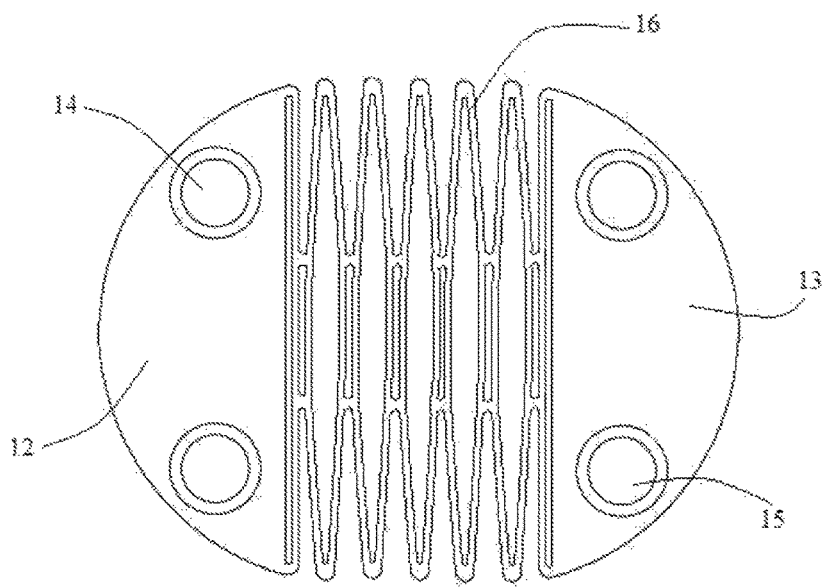

FIGS. 8 through 10 illustrate an exemplary cranial fixation device with a circular shape, in accordance with an embodiment of the present invention. FIG. 8 is a diagrammatic top view of the device in a contracted position. FIG. 9 is a diagrammatic side view of the device in the contracted position, and FIG. 10 is a diagrammatic top view of the device in an expanded position. The circular shape of the device may be well suited to cover a burr hole skull defect. In the present embodiment, the device comprises of a first anchor portion 12 with bone fastener holes 14 and a second anchor portion 13 with bone fastener holes 15. Anchor portions 12 and 13 are connected by an intermediate component 16. Intermediate component 16 comprises a plurality of parallel tension springs that reversibly expand or contract dependent upon the pressure exerted on the anchor portion attached to the bone flap. Typically, intermediate component 16 is designed to expand when the ICP exceeds 20 to 25 mm Hg and to retract when the ICP is normal (i.e., less than 15 to 20 mmHg). It is contemplated that some alternate embodiments may be implemented to expand and retract at different pressures in order to accommodate applications in which the ICP may be higher or lower than normal.

FIGS. 11 through 13 illustrate an exemplary cranial fixation device with a circular shape, in accordance with an embodiment of the present invention. FIG. 11 is a diagrammatic top view of the device in a contracted position. FIG. 12 is a perspective side view of the device in the contracted position attached to a skull 54 on one side and a bone flap 55 on the other side. FIG. 13 is a diagrammatic top view of the device in an expanded position. In the present embodiment, the device comprises anchor portions 17 and 18 with bone fastener holes 21 and 22, respectively, separated by a space 25 and anchor portions 19 and 20 with bone fastener holes 23 and 24, respectively, separated by a space 26. Anchor portions 17 and 18 are connected with anchor portions 19 and 20 by an intermediate component 27. Intermediate component 27 comprises a plurality of tension springs that reversibly expand or contract dependent upon the pressure exerted on one anchor portion versus the other. The four anchor portions 17, 18, 19, and 20 can move independently of each other's positions, thereby allowing for a particularly flexible device.

In the various embodiments described in the foregoing, the configuration of the anchor portions come together to form substantially rectangular, square or circular shapes when in a compressed position. Those skilled in the art will readily recognize, in light of and in accordance with the teachings of the present invention, that some alternate embodiments may be implemented with anchor portions with a multiplicity of suitable configurations such as, but not limited to, oval configurations, semi-circle configurations, semi-oval configurations, C-shapes, L-shapes, T-shapes, X-shapes, Y-shapes, Z-shapes, fan shapes, configurations in which the anchor portions differ from each other in size and/or shape, or any other configuration able to connect a skull to a bone flap. Some alternate embodiments may comprise multiple intermediate components that may or may not be joined to opposite anchor portions. Furthermore, the cranial fixation devices described in the foregoing are illustrated by way of example with unitary construction, such that the anchor portions and intermediate components are formed from a single piece material. Some alternative embodiments contemplate that the components of the cranial fixation devices can be non-integral such that the components may be attached to and/or coupled to other components of the device. The intermediate components illustrated by way of example in the forgoing comprise substantially parallel tension springs that are connected at the ends or connected at the ends and the middle portions. The expandable intermediate component in some alternate embodiments may comprise a multiplicity of suitable expansion means including, without limitation, tension springs attached at the middle only, tension springs with an accordion-like configuration, expandable mesh material, crosslinks, compressed O-shaped, U-shaped, V-shaped, X-shaped or W-shaped members that expand, a plurality of cutouts, a single tension spring, an elastomeric component, a spring, hinged connectors, coiled wire, chain, sliding connectors, an elastic cord, or a combination thereof.

It is contemplated that cranial fixation devices according to many practical embodiments of the present invention may be made of a multiplicity of suitable materials including, without limitation, metals such as, but not limited to, titanium or titanium alloy for MRI imaging compatibility. Some embodiments may be made of materials that are typically absorbed by the body over time including, without limitation, allograft, xenograft bone, or a bioresorbable material such as, but not limited to, polyesters, poly amino acids, polyanhydrides, polyorthoesters, polyurethanes, polycarbonates, homopolymers, copolymers of poly lactic acid and poly glycolic acid, copolyesters of e-caprolactone, trimethylene carbonate, or para-dioxanone. Alternatively, some embodiments may be made of a radiolucent material such as, but not limited to, polyetheretherketone (PEEK), polyaryletherketone (PEAK), high molecular weight polyethylene, carbon fiber, polyurethane, plastic, or a combination of plastic and metal to reduce CT and MRI imaging artifact. The expandable material of the intermediate components in some embodiments may be made of various different materials such as, but not limited to, silicone, rubber, ethylene propylene compounds, flourocarbon, polyurethane, titanium, other metal components designed to reversibly expand and/or contract, etc. In many practical embodiments, the thickness of the device generally ranges from 0.3 mm to 20 mm. The size of the anchor portions generally range from 6 mm to 40 mm. The expandable intermediate component of the cranial fixation device is typically capable of reversibly expanding from 1 to 1000% of its contracted size. While the above-mentioned size ranges of the device components reflect many practical embodiments, some alternate embodiments may comprise components outside of the aforementioned ranges.

In some alternate embodiments, the cranial fixation device comprises anchor portions that are relatively small in size in relation to an expandable intermediate component that connects the anchor portions. FIGS. 14 and 15 illustrate an exemplary cranial fixation device, in accordance with an embodiment of the present invention. FIG. 14 is a diagrammatic top view of the device in a contracted position, and FIG. 15 is a diagrammatic top view of the device in an expanded position. In the present embodiment, the device comprises a first anchor portion 27 with a bone fastener hole and a second anchor portion 28 with a bone fastener hole. Anchor portions 27 and 28 are connected by an expandable intermediate component 29. Intermediate component 29 comprises a series of compressed, oval-shaped tension springs, as shown by way of example in FIG. 14, which are capable of reversibly expanding into wider diamond shapes, as shown by way of example in FIG. 15.

Figure 16:
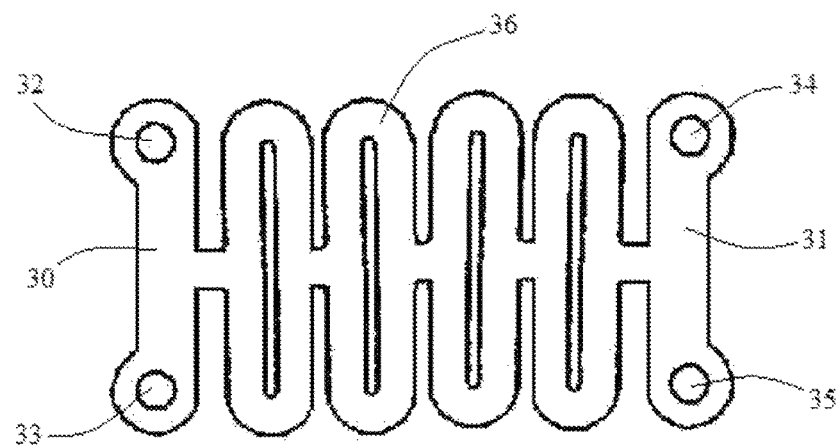
FIGS. 16 and 17 illustrate an exemplary cranial fixation device, in accordance with an embodiment of the present invention.
Figure 17:
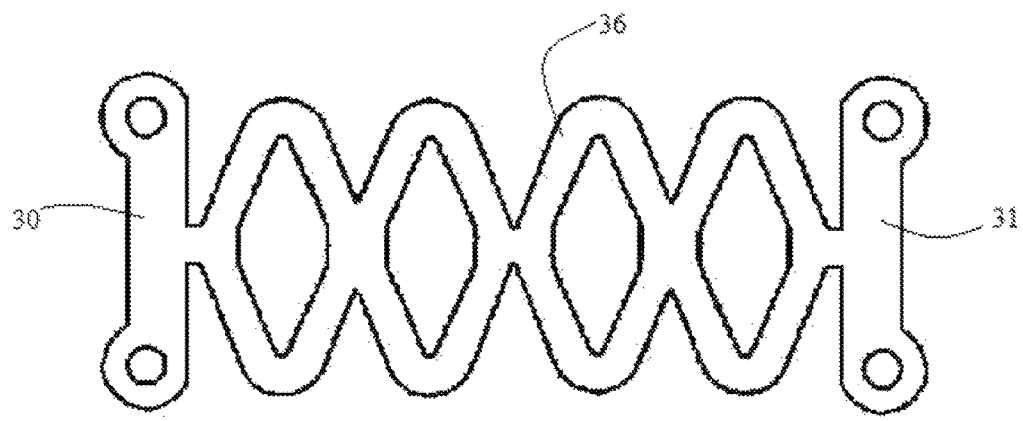

FIGS. 16 and 17 illustrate an exemplary cranial fixation device, in accordance with an embodiment of the present invention. FIG. 16 is a diagrammatic top view of the device in a contracted position, and FIG. 17 is a diagrammatic top view of the device in an expanded position. In the present embodiment, the device comprises a first anchor portion 30 with bone screw holes 32 and 33 and a second anchor portion 31 with bone screw holes 34 and 35. An intermediate component 36 comprising a series of compressed, oval-shaped tension springs connects anchor portions 30 and 31.

Figure 18:
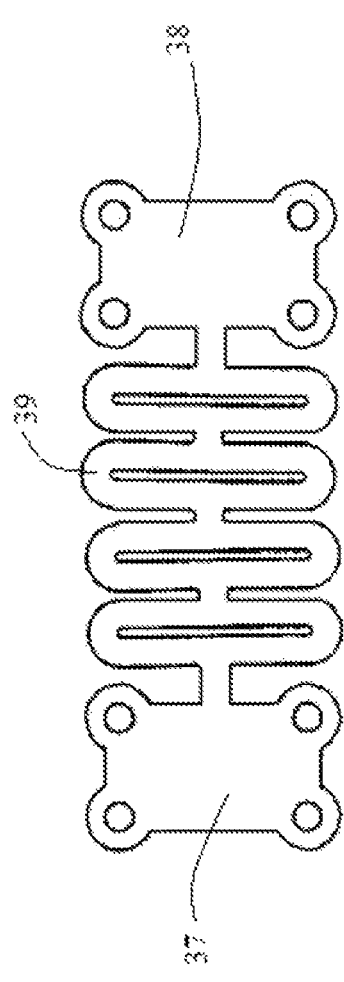
FIGS. 18 and 19 illustrate an exemplary cranial fixation device, in accordance with an embodiment of the present invention.
Figure 19:
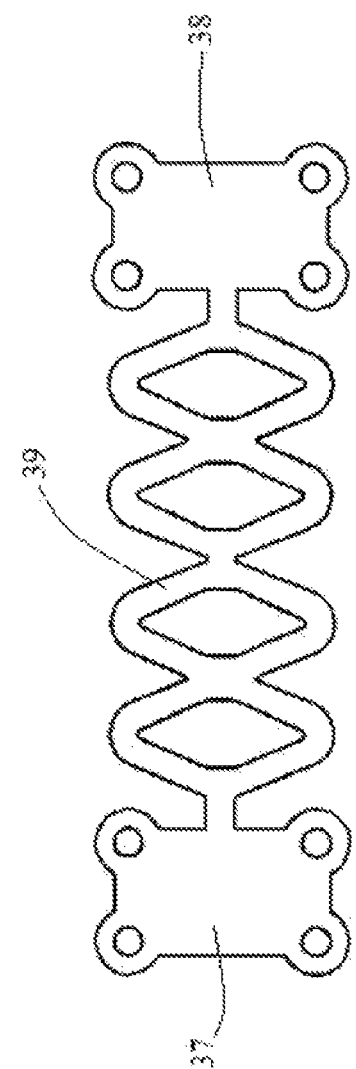

FIGS. 18 and 19 illustrate an exemplary cranial fixation device, in accordance with an embodiment of the present invention. FIG. 18 is a diagrammatic top view of the device in a contracted position, and FIG. 19 is a diagrammatic top view of the device in an expanded position. In the present embodiment, anchor portions 37 and 38 each comprise four bone fastener holes and are connected by a series of elastic tension spring members in an intermediate component 39. It is contemplated that cranial fixation devices similar to the devices illustrated by way of example in FIGS. 14 through 19 may comprise more or fewer holes for bone fasteners or bone screws, tension springs of various different shapes, other types of expanding means, etc. Furthermore, some alternate embodiments may be implemented in various different configurations such as, but not limited to, rectangular configurations with four anchor portions and four intermediate components, triangular configurations, L-shaped configurations, T-shaped configurations, V-shaped configurations, X-shaped configurations, Z-shaped configurations, etc.

Figure 20:
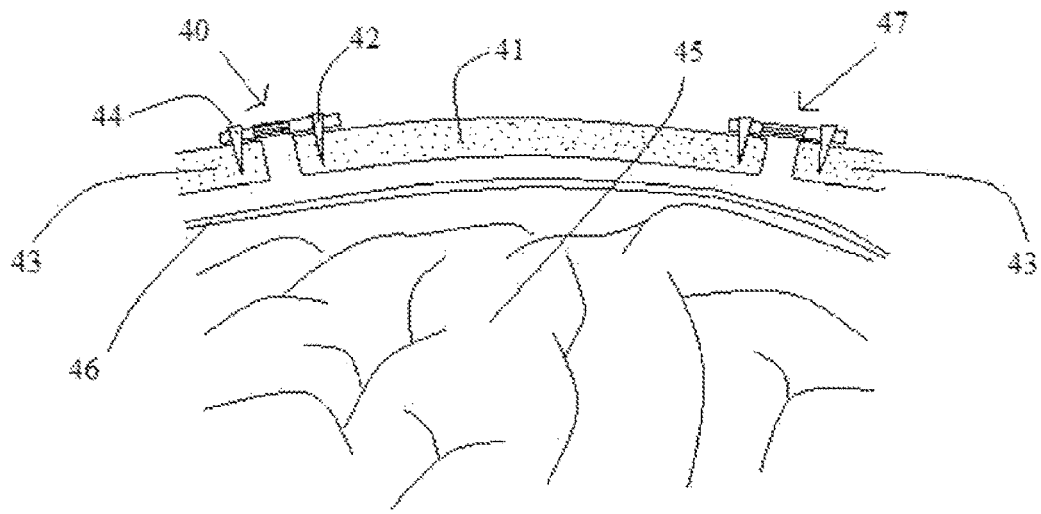
FIGS. 20 and 21 are cross sectional side views of exemplary cranial fixation devices attached to a skull and a bone flap for a decompressive craniotomy, in accordance with an embodiment of the present invention.
Figure 21:
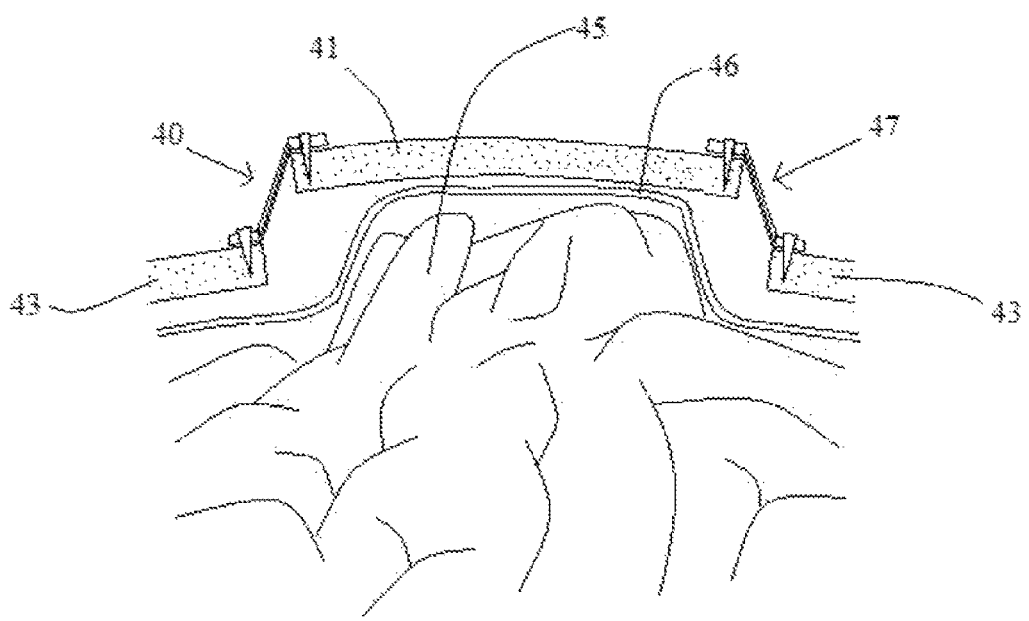

FIGS. 20 and 21 are cross sectional side views of exemplary cranial fixation devices 40 and 47 attached to a skull 43 and a bone flap 41 for a decompressive craniotomy, in accordance with an embodiment of the present invention. FIG. 20 shows a brain 45 in a non-swollen state, and FIG. 21 shows brain 45 in a swollen state. In the present embodiment, cranial fixation device 40 is attached to bone flap 41 with a screw 42 and is attached to skull 43 with a screw 44. The length of screws 42 and 44 can range from 4 mm to 20 mm. In some alternate embodiments, the cranial fixation devices may be attached to the skull and bone flap with larger or smaller screws, with spikes, with a combination of screws on one anchor portion and spikes on the other anchor portion, etc. In other alternate embodiments, the cranial fixation device may comprise various different attachment means such as, but not limited to, clamps which are attached to the skull and/or bone flap, self-tapping screws, selfdrilling screws, pins, rivets, wires, sutures, clamps, claws, spikes, hooks, adhesives, etc. In addition, in some applications the fixation devices may be attached to the skull with attachment means and left unattached to the bone flap to provide greater mobility of the bone flap. Referring to FIGS. 20 and 21, typically two or more cranial fixation devices 40 and 47 are used to affix bone flap 41 to skull 43. Alternatively, a cranial fixation device can be placed on one side of the bone flap and a hinge device can be placed on the other side to provide a similar yet potentially limited decompressive craniotomy.

Referring to FIG. 20, brain 45 and a dura 46 are in a normal position. Referring to FIG. 21, with the development of swelling of brain 45 or an increase in ICP from a hemorrhage or other cause, brain 45 pushes against hone flap 41. The pressure on bone flap 41 expands the intermediate components of cranial fixation devices 40 and 47, thereby allowing the anchor portions attached to bone flap 41 to move outward relative to the anchor portions attached to skull 43 to accommodate the swelling of brain 45. Referring to FIG. 20, once the swelling subsides, cranial fixation devices 40 and 47 draw back to their contracted positions, and bone flap 41 moves back towards skull 43.

Figure 22:
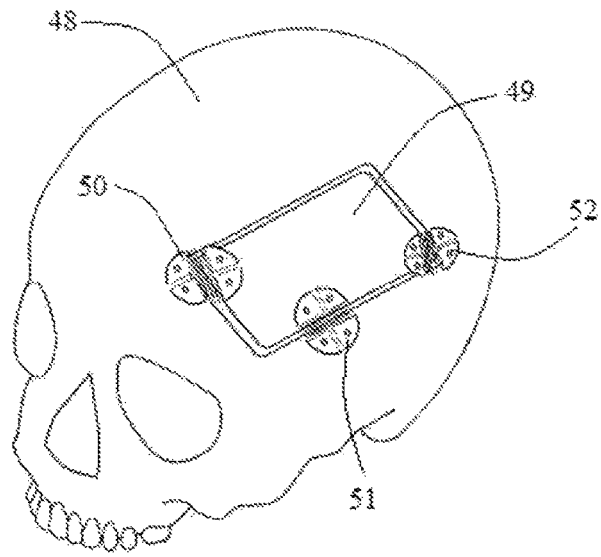
FIGS. 22 and 23 are side perspective views of exemplary cranial fixation devices in place to secure a bone flap to a skull by a decompressive craniotomy, in accordance with an embodiment of the present invention.
Figure 23:
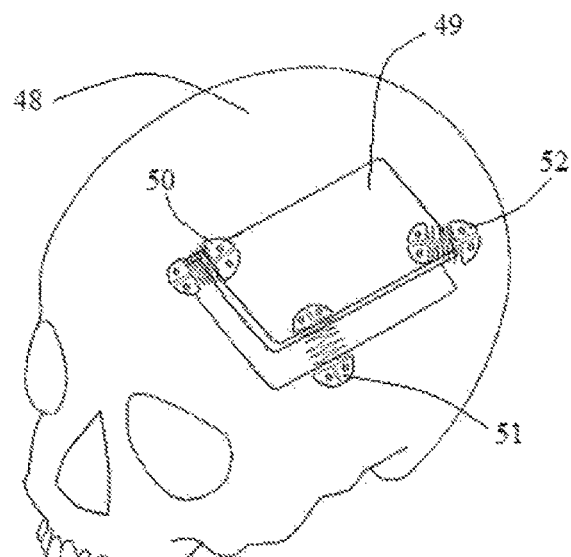

FIGS. 22 and 23 are side perspective views of exemplary cranial fixation devices 50, 51 and 52 in place to secure a bone flap 49 to a skull 48 by a decompressive craniotomy, in accordance with an embodiment of the present invention. FIG. 22 shows the normal position of bone flap 49, and FIG. 23 shows bone flap 49 shifted outwards relative to skull 48 to accommodate an increase in the pressure inside skull 48. In the present embodiment, after a craniotomy bone flap 49 is attached to skull 48 with cranial fixation devices 50, 51, and 52. Devices 50, 51 and 52 are spaced apart to provide adequate support and to generally prevent bone flap 49 from sinking below the surface of skull 48. Flexible intermediate components of devices 50, 51, and 52 enable bone flap 49 to move outward relative to skull 48 to accommodate an increase in ICP and to retract when any such pressure subsides. Normal ICP is typically less than 20 mm Hg, and with any brain swelling or hemorrhage ICP can increase to greater than 20 mm Hg. Referring to FIG. 22, with an increase in ICP above the normal range, cranial fixation devices 50, 51 and 52 are designed to enable the intermediate components to lengthen into an extended position from a contracted position and therefore enable the two anchor portions of each device 50, 51 and 52 to move apart, thereby allowing bone flap 49 to move outwards from skull 48 in a constrained manner to accommodate the higher ICP. Referring to FIG. 23, once ICP returns to below 20 mm Hg, the intermediate components retract and position bone flap 49 downwards to substantially the same level as skull 48.

Figure 24:
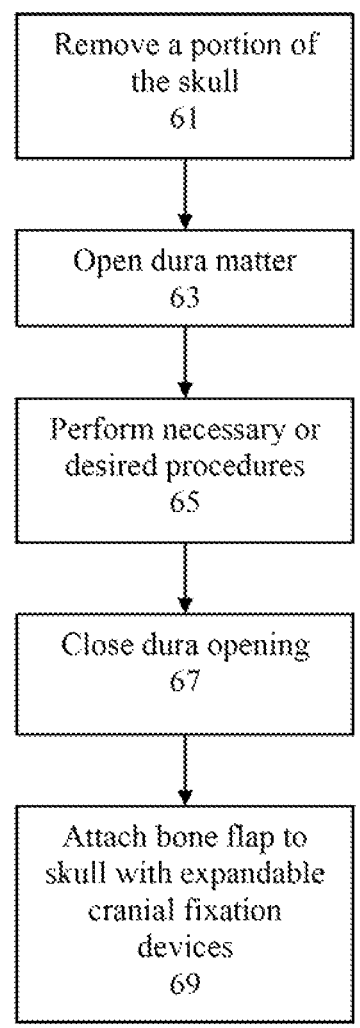
FIG. 24 is a flowchart illustrating an exemplary method for a decompressive craniotomy, in accordance with an embodiment of the present invention.

FIG. 24 is a flowchart illustrating an exemplary method for a decompressive craniotomy, in accordance with an embodiment of the present invention. A decompressive craniotomy is typically performed to reduce increases in the ICP of a patient, which may be caused by a variety of factors or occurrences. In the present embodiment, the process begins in step 61 by removing a portion of the skull. In step 63 the dura matter covering the brain is opened, thereby allowing the swollen brain to herniate outwards through the surgical skull defect. In general, it is believed that the larger the bone flap removed in step 61 is, the more ICP is reduced. With the removal of the hone flap and the opening of the dura matter, the practitioners may take this opportunity to perform necessary or requested procedures on the brain of the patient in step 65 such as, but not limited to, hematoma evacuation, biopsies, tumor removal, repairing an injury, placing a shunt, etc. The dural opening is typically closed in step 67. The dural closure material is often a collagen matrix that allows for expansion. Alternatively, other dural substitutes may be used such as, but not limited to, grafts made from autograft, allograft, or xenograft material or grafts taken from cows, pigs, cadavers, etc. In an alternate embodiment, this step may be skipped, and the dura may be left open. In the present embodiment, the bone flap is replaced and attached to the skull by one or more expandable cranial fixation devices in step 69. Typically, two more of expandable cranial fixation devices are used to achieve this form of decompressive craniotomy. Alternatively, an expandable cranial fixation device can be placed on one side of the bone flap and a hinge device can be placed on the other side. In the present embodiment, the anchor portions of the cranial fixation devices are positioned on the surfaces of the skull and the bone flap to hold the bone flap substantially level with the skull when the expandable intermediate componeths of the fixation devices are contracted and to allow external movement of the bone flap relative to the skull in case of an increase in ICP. When an increase in ICP exceeds the normal range, the bone flap is pushed outwards and causes the expandable intermediate components of the cranial fixation devices to stretch into an extended position. The external movement of the bone flap increases the intracranial space to accommodate the increase in ICP and provides for a decompressive craniotomy. Following normalization of the ICP, the bone flap is compressed back towards the skull by the cranial fixation devices.

Although the application for the cranial fixation device described in the present embodiment is for fixation of the bone flap to the skull following a craniotomy and to provide for a decompressive craniotomy to treat increased ICP, cranial fixation devices according to various embodiments of the preset invention may be used to treat ICP resulting from various different causes such as, but not limited to, traumatic injury, subdural hemorrhage, epidural hemorrhage, subarachnoid hemorrhage, intra-ventricular hemorrhage, brain hemorrhage, ischemic stroke, hemorrhagic stroke, hypoxia, tumor, infection, brain swelling, or seizure, etc. Moreover, some embodiments may be used in different types of applications including, but not limited to, covering a burr hole, repairing a skull fracture, treating congenital cranial skull defects such as, but not limited to, craniosynostosis, etc.

Those skilled in the art will readily recognize, in light of and in accordance with the teachings of the present invention, that any of the foregoing steps may be suitably replaced, reordered, removed and additional steps may be inserted depending upon the needs of the particular application. Moreover, the prescribed method steps of the foregoing embodiments may be implemented using any physical and/or hardware system that those skilled in the art will readily know is suitable in light of the foregoing teachings. For any method steps described in the present application that can be carried out on a computing machine, a typical computer system can, when appropriately configured or designed, serve as a computer system in which those aspects of the invention may be embodied.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Having fully described at least one embodiment of the present invention, other equivalent or alternative methods of providing an expandable fixation device according to the present invention will be apparent to those skilled in the art. The invention has been described above by way of illustration, and the specific embodiments disclosed are not intended to limit the invention to the particular forms disclosed. For example, the particular implementation of the anchor portions may vary depending upon the particular type of item on which the anchor portions are to be attached. The anchor portions described in the foregoing were directed to cranial implementations that attach to the skull; however, similar techniques are to provide expandable fixation devices with various different types of anchor portions for use in different areas of the anatomy such as, but not limited to, ribs, vertebrae, other bones, soft tissue, etc. Non-cranial implementations of the present invention are contemplated as within the scope of the present invention. The invention is thus to cover all modifications, equivalents, and alternatives falling within the spirit and scope of the following claims.

Claim elements and steps herein may have been numbered and/or lettered solely as an aid in readability and understanding. Any such numbering and lettering in itself is not intended to and should not be taken to indicate the ordering of elements and/or steps in the claims.

What is claimed is:

1. A fixation device configured for decompressive craniotomy procedures, the fixation device comprising:
   a first end further comprising a first set of two anchor portions configured to join a first bone portion, wherein the two anchor portions of the first set are unconnectedly spaced apart;
   a second end further comprising a second set of one or more anchor portions configured to join a second bone portion; and
   an intermediate component integrally affixed to and extending between the first end and the second end, the intermediate component can expand and contract enabling inward and outward relative movement between the first bone portion and the second bone portion, and enabling each of the two anchor portions of the first set and each of the one or more anchor portions of the second set to move independently of each other, wherein
   each of the two anchor portions of the first set includes a linear side surface, and
   the linear side surface of one anchor portion of the two anchor portions of the first set faces the linear side surface of another anchor portion of the two anchor portions of the first set with a gap therebetween.

2. The fixation device as recited in claim 1, further comprising bone fastener components being configured to join the first set of two anchor portions to the first bone portion and to join the second set of one or more anchor portions to the second bone portion.

3. The fixation device as recited in claim 1, wherein each of the two anchor portions of the first set and each of the one or more anchor portions of the second set comprises at least one aperture being configured to receive at least one bone fastener component.

4. The fixation device as recited in claim 1, wherein the intermediate component comprises at least one spring member.

5. The fixation device as recited in claim 1, wherein the intermediate component comprises a plurality of elastic tension spring members.

6. The fixation device as recited in claim 1, wherein the first set of two anchor portions, the second set of one or more anchor portions and the intermediate component are formed from a single piece of material.

7. The fixation device as recited in claim 1, wherein the intermediate component comprises a plurality of spring members joined to the first set of two anchor portions and the second set of one or more anchor portions.

8. The fixation device as recited in claim 1, wherein the fixation device comprises a material generally absorbable by a body.

9. A fixation device comprising:
   a first end further comprising a first set of two anchor portions configured to join to a skull bone, each of the two anchor portions of the first set comprising at least one aperture, wherein the two anchor portions of the first set are unconnectedly spaced apart;
   a first set of bone fastener components configured to join the first set of two anchor portions to the skull bone at at least one of the apertures;
   a second end further comprising a second set of one or more anchor portions configured to join to a bone flap, each of the one or more anchor portions of the second set comprising at least one aperture;
   a second set of bone fastener components configured to join the second set of one or more anchor portions to the bone flap at at least one of the apertures; and
   an intermediate component integral to and extending between the first set of two anchor portions and the second set of one or more anchor portions, the intermediate component configured to expand and contract to enable outward and inward movement of the bone flap in response to fluctuations in intracranial pressure, and enabling each of the two anchor portions of the first set and each of the one or more anchor portions of the second set to move independently of each other, wherein
   each of the two anchor portions of the first set includes a linear side surface, and
   the linear side surface of one anchor portion of the two anchor portions of the first set faces the linear side surface of another anchor portion of the two anchor portions of the first set with a gap therebetween.

10. The fixation device as recited in claim 9, wherein the intermediate component comprises a series of elastic tension spring members.

11. The fixation device as recited in claim 9, wherein the first set of two anchor portions, the second set of one or more anchor portions and the intermediate component are formed from a single piece of material.

12. The fixation device as recited in claim 9, wherein the intermediate component comprises a plurality of spring members joined to the first set and second set of anchor portions.

13. The fixation device as recited in claim 9, wherein the fixation device comprises a material generally absorbable by a body.

14. A surgical fixation device comprising:
   a first end further comprising a first set of two anchor portions configured to join to a skull bone, wherein the two anchor portions of the first set are unconnectedly spaced apart;
   a second end further comprising a second set of one or more anchor portions configured to join a bone flap; and
   an intermediate component integrally extending between the first set of two anchor portions and the second set of one or more anchor portions, the intermediate component being responsive to changes in intracranial pressure, and enabling each of the two anchor portions of the first set and each of the one or more anchor portions of the second set to move independently of each other, wherein each of the two anchor portions of the first set includes a linear side surface, and the linear side surface of one anchor portion of the two anchor portions of the first set faces the linear side surface of another anchor portion of the two anchor portions of the first set with a gap therebetween.

15. The surgical fixation device of claim 14, wherein the intermediate component moves in a range between a first position where the bone flap is higher relative to the skull bone, and a second position wherein the bone flap is in line relative to the skull bone.

16. The surgical fixation device of claim 14, wherein each of the two anchor portions of the first set comprises at least one aperture.

17. The surgical fixation device of claim 14, wherein each of the one or more anchor portions of the second set comprises at least one aperture.

18. The fixation device of claim 1, wherein
the one more anchor portions of the second set is at least two anchor portions, and
the at least two anchor portions of the second set are unconnectedly spaced apart.

19. The fixation device of claim 9, wherein
the one more anchor portions of the second set is at least two anchor portions, and
the at least two anchor portions of the second set are unconnectedly spaced apart.

20. The surgical fixation device of claim 14, wherein
the one more anchor portions of the second set is at least two anchor portions, and
the at least two anchor portions of the second set are unconnectedly spaced apart.

* * * * *